(12) United States Patent
Melikechi et al.

(10) Patent No.: US 6,755,647 B2
(45) Date of Patent: Jun. 29, 2004

(54) PHOTOCURING DEVICE WITH AXIAL ARRAY OF LIGHT EMITTING DIODES AND METHOD OF CURING

(75) Inventors: Noureddine Melikechi, Dover, DE (US); Ranjit D. Pradhan, Wyoming, DE (US)

(73) Assignee: New Photonics, LLC, Dover, DE (US)

( * ) Notice: Subject to any disclaimer, the term of this patent is extended or adjusted under 35 U.S.C. 154(b) by 18 days.

(21) Appl. No.: 09/842,500

(22) Filed: Apr. 26, 2001

(65) Prior Publication Data
US 2002/0187454 A1 Dec. 12, 2002

(51) Int. Cl.[7] .................................................. A61C 3/00
(52) U.S. Cl. ......................................... 433/29; 433/215
(58) Field of Search ........................ 433/29, 215, 229; 606/13, 16; 362/118, 119, 120

(56) References Cited

U.S. PATENT DOCUMENTS

| | | | |
|---|---|---|---|
| 4,112,335 A | 9/1978 | Gonser | 315/241 R |
| 4,229,658 A | 10/1980 | Gonser | 250/504 H |
| 4,358,344 A | 11/1982 | Sass et al. | 201/4 |
| 5,147,204 A | 9/1992 | Patten et al. | 433/229 |
| 5,420,768 A * | 5/1995 | Kennedy et al. | 362/119 |
| 5,616,141 A | 4/1997 | Cipolla | 606/15 |
| 5,634,711 A | 6/1997 | Kennedy et al. | 362/119 |
| 5,711,665 A | 1/1998 | Adam et al. | 433/9 |
| 5,879,159 A | 3/1999 | Cipolla | 433/29 |
| 5,885,082 A | 3/1999 | Levy | 433/215 |
| 6,077,073 A * | 6/2000 | Jacob | 433/29 |
| 6,099,520 A | 8/2000 | Shimoji | 606/2 |
| 6,102,696 A * | 8/2000 | Osterwalder et al. | 433/29 |
| 6,159,005 A | 12/2000 | Herold et al. | 433/29 |
| 6,171,105 B1 | 1/2001 | Sarmadi | 433/29 |
| 6,200,134 B1 * | 3/2001 | Kovac et al. | 433/29 |

FOREIGN PATENT DOCUMENTS

WO    WO 99/35995    7/1999    ........... A61C/13/15

* cited by examiner

Primary Examiner—Nicholas D. Lucchesi
(74) Attorney, Agent, or Firm—Michael W. Ferrell

(57) ABSTRACT

A device for curing a photosensitive dental composition curable by way of irradiation with light of predetermined wavelength includes a power supply; and a radiation source coupled to the power supply and powered thereby, the radiation source having a radiation output and including an axial array of light emitting diodes. The light emitting diodes are mounted about an assembly axis defined thereby at a plurality of axial distances from said radiation output of the radiation source and being further characterized in that the plurality of light emitting diodes are directed along a plurality of divergent paths such that a position insensitive optical field is generated for curing the dental composition.

23 Claims, 7 Drawing Sheets

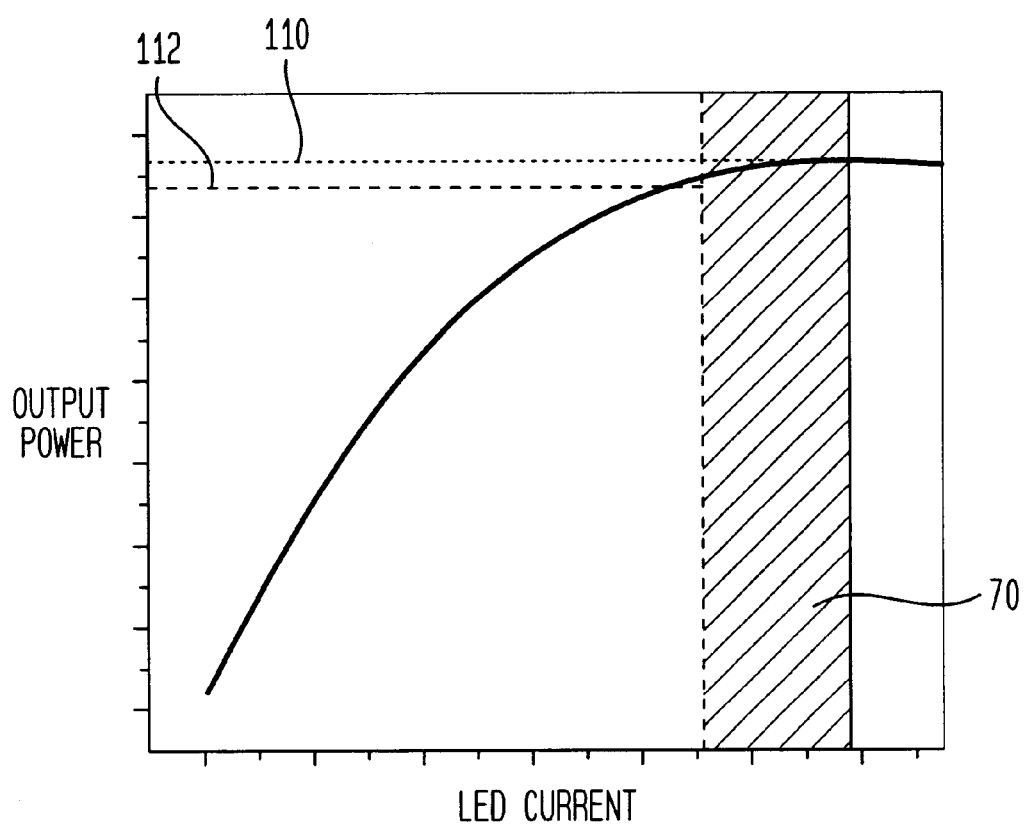

PHOTOCURING DEVICE WITH AXIAL ARRAY OF LIGHT EMITTING DIODES AND METHOD OF CURING

TECHNICAL FIELD

The present invention relates generally to photocurable dental compositions and more specifically to a device provided with an axial array of light emitting diodes directed along a plurality of divergent paths such that a position insensitive optical field is generated.

BACKGROUND

Certain polymeric materials useful in the field of dentistry for adhesion, sealing and restoration may be cured or hardened upon exposure to a source of radiation. Such photoactive materials are known as "photo-curable dental compositions" and generally harden when exposed to radiation having wavelengths in the visible range. Photo-cured dental compositions are convenient for use by a dentist because the curing process can be initiated when the dental composition has been accurately placed in its proper position. A source of radiation energy positioned proximate to the material to be hardened, for example an appropriate amount of composition placed inside a tooth cavity, is activated to initiate polymerization and subsequent curing of the composition to secure the repair. Early methods for curing photosensitive dental compositions included dental guns and other apparatuses for producing concentrated beams of UV radiation. See U.S. Pat. Nos. 4,112,335 and 4,229,658, for example. Later, visible light curable dental compositions were used and dental radiation guns for producing concentrated visible light were provided like that disclosed in U.S. Pat. Nos. 4,385,344 and 6,171,105. However, a relatively high divergence about 25 degrees of the light beam from such visible light sources reduces penetration into the tooth structure, leading to their relative inefficiency and unreliability for photo-curing dental composition that are thicker than about two millimeters.

Photo-curable dental materials have also been developed that are hardened by exposure to radiant energy in a pre-selected spectral range. Typically, a photo-activated chemical reaction in many photo-curable dental materials is initiated by application of a high intensity blue light having a wavelength of 400–500 nanometers. Since the light sources employed typically produce the entire visible light spectrum as well as some non-visible radiation, a reflector is coated to reflect only visible light, and the filters are selected to substantially block non-visible radiation and visible light other than blue light in the range of 400–500 nanometers, in order to produce the desired range of radiation, as shown for example in U.S. Pat. No. 5,147,204. Other high power arc sources, such as the one disclosed in U.S. Pat. No. 5,879,159, produce filtered wavelengths in the 430–505 nanometer range. Laser based radiation sources have also been employed, using for example, an argon-ion laser producing either specific wavelengths or their combinations in the 450–514 nanometer range. See U.S. Pat. No. 5,616,141. U.S. Pat. No. 6,099,520 discloses a portable, cordless, hand-held device that uses a diode-pumped microchip laser emitting radiation at 480 nm.

There are several disadvantages in using light curing apparatuses of the prior art like those discussed above. Commercially available dental light guns that use metal halide or plasma ark lamps often include an elongated, slender light guide such as a bundle of optical fibers having a free end that can be positioned close to the photo-curable material in order to direct light to the material from a light source located outside the oral cavity. The bundle of optical fibers is an added component that reduces the efficiency of the light reaching the curing site. Thus, because of the relatively large size of the dental gun within a patient's mouth, a degree of physical discomfort is introduced to the patient as well as to the dentist who must hold the gun steady for about one minute. These sources produce all visible and some non-visible wavelengths and use band pass filters to admit wavelengths of interest. The result is a heating of the device that must be cooled using a cooling fan or other means.

Second, the area illuminated by conventional blue-filtered metal-halide radiation is usually in the range of about a ½-inch diameter circle and over a typical curing cycle of about 60 seconds. The relatively high energy output and beam divergence of such dental guns leads to the possibility of increased heating of the pulp tissue which is sensitive to small changes in temperature.

The argon laser sources are bulky and transport of laser light from the argon laser source to the curing site can only be accomplished by a long fiber-optic delivery system. The technology of either the argon laser or the diode-pumped microchip laser is complex and prevents inexpensive implementation. Their maintenance and repairs are also expensive Lasers are intrinsically inefficient devices meaning that a very small portion of the electrical energy is finally converted to useful light. Furthermore there is the danger of accidental exposure of coherent laser radiation to the eye of either the dentist or the patient during the dental procedure resulting in a damage that could be greater than that resulting from incoherent radiation.

In addition, when dental compositions are cured in place within a cavity for instance, after curing an amount of shrinkage of about 2.5–3.0% occurs leaving a gap within the area being treated; such shrinkage is so deleterious that any small reduction in shrinkage is desirable.

Furthermore, in tests of cure depth uniformity of standardized compositions, it was found that a high percentage (46%) of curing lights used in private dental offices are unsuitable for use when tested against manufacture's recommendations using a curing radiometer or a heat radiometer, due in part to the loss of output of the light source in use [J Dent Mar. 27, 1999 (3):235–41]. Finally, due to the expenses of combining a laser or metal-halide radiation source, focusing elements, power sources, etc., significant expense are involved in purchasing and using dental guns. Conventional dental curing devices are therefore seen to have shortcomings including uncomfortable use, unreliable curing and relatively high expense.

U.S. Pat. No. 4,385,344 discloses a dental gun device for production of light in the low visible range for photo-curing dental compositions, the device comprising a tungsten halogen lamp with a concentrating reflector, which reflects visible light and passes middle and far infrared wavelengths. A dichroic heat reflecting filter which passes light from 400 to 700 nm and reflects energy in the visible red and near infrared wavelengths back to the lamp envelope, enhances lamp halogen cycle efficiency. The dichroic heat-reflecting filter is followed by a dielectric filter, which provides a high efficiency bandpass at the desired visible range. A fiber optic light guide is positioned to receive the focused and filtered light and to transmit it to a reduced surface light-applying tip at the end of the handpiece. The fiber light guide is encased in a specially designed sheathing, which provides protection to the optical fibers and carries two electrical conductors which are connected between a control switch on the handpiece and the power supply for the lamp.

U.S. Pat. No. 5,147,204 is representative of conventional blue-light filtered dental guns. This patent discloses a blue light emitting apparatus for curing photo-curable dental material including a handpick having a housing, a depending handle and a detachable light guide. The light guide is received in a head connected to the housing. A source of tungsten-halogen light is coupled to the housing, and a light guide is detachably connected to the head for communication with the source of light. Since the tungsten-halogen light produces the entire visible light spectrum as well as some non-visible radiation, a reflector is coated to generally reflect only visible light, and a blue-pass filter and a heat filter are selected to substantially block non-visible radiation and visible light other than blue light in the range of 400–500 nanometers.

Still further devices and techniques have been proposed as noted below.

There is shown in U.S. Pat. No. 5,420,768 to Kennedy, for instance, a portable photo-curing device that has a light emitting diode matrix which is energized with battery power. The '768 patent notes in Column 2 that LEDs of various selected colors may be formed on the module by using selected color dyes so that the emitted light is a pure white light or a combination of selected color lights to provide a predetermined photo curing effect. The light emitted by the LEDs may have a peak wavelength of 470 nm which is used for photo curing purposes.

U.S. Pat. No. 5,634,711 to Kennedy et al. discloses a portable light emitting device suitable for medical and industrial photo curing. It is noted in the '711 patent that various applications require different light dosage values. For example, it is noted in Column 1, lines 39 and following that light dosage values in the range of up to 400 mW/cm$^2$ are typically required for dental applications. On the other hand, a medical application such as photodynamic therapy of psoriasis and basal cells requires much lower power typically in the range of up to 100 mW/cm$^2$. The device according to the '711 patent includes generally a power supply, a housing, and a substrate upon which a plurality of light emitting diodes are mounted. It can be seen from FIGS. 1 and 6 of the patent that the LED array is generally planar and that the device typically includes an optical assembly such as a fiber optic taper. Here again, the LED can comprise "blue" LEDs with a spectral emission in the 470 nanometer range. Typically, the LEDs are driven by a pulsed power supply in order to minimize heat generation.

U.S. Pat. No. 5,711,655 to Adam et al. discloses a method and apparatus for bonding orthodontic brackets to teeth. The subject device includes a base with a central opening and a body with a passage aligned with that opening. A curing light assembly includes an outer end portion that is removably received in the passage for curing adhesive beneath the central section of the bracket body. Once the adhesive beneath the central section of the bracket body is cured to temporarily tack the bracket base to the patient's tooth adhesive extruded from the peripheral edge of the bracket base can be readily removed without dislodging the bracket from its intended position. The device can be used to create a temporary "tack" bond while another device is used to fully cure the composition. See Col. 8–9. A curing light assembly optionally includes a focusing lens for an LED emitter which may be a dome shaped lens that covers the diode. See Column 6, lines 45 and following.

U.S. Pat. No. 6,102,696 to Osterwalder et al. discloses a self-contained light source for curing light initiated resins used to coat teeth as veneers and fill cavities and chips in teeth in aesthetic or restorative procedures. The source includes an elongated container holding a battery and an electronic compartment in one end and a light emitting window at the other. A plurality of closely spaced light emitters, typically light emitting diodes or laser diodes are arrayed in a radial or arcuate configuration to direct light to a common focal point. The light is directed out of the container toward a tooth bearing the resin to be cured to a hard stable state. The light emitters produce light in a region of the spectrum to which the resin curing initiator is sensitive, typically blue light. It can be seen from FIGS. 2 and 3 of the '696 patent that LEDs are typically arrayed in an arcuate configuration about a focal point 38. The apparatus is reported to be useful for curing dental resins including a 1:1 mixture by weight of bis-phenol-2 bis (2-hydroxypropyl) methacrylate and tri (ethylene glycol) dimethacrylate monomers. The resinous mixture may further include a camphorquinone photoinitiator and a tertiary amine reducing agent. Fillers such as silica particles and colorants are typically included to achieve the desired hardness level and color.

U.S. Pat. No. 6,159,005 to Harold et al. discloses an apparatus for photopolymerizing synthetic materials, specifically dental materials containing camphorquinone or phosphine oxide as photoinitiators includes a light source constituted by a semiconductor base solid state radiation emitter which emits in the blue spectral range. Since the radiation emitter emits in a relatively limited spectral range excess heat radiation is avoided. The overall device is formed as a relatively small lightweight device with a built in battery. The device further includes a light-conducting rod in order to direct radiation to the desired location. According to the '005 patent an essential photoinitiator in dental materials is typically camphorquinone or phosphine oxide which absorbs a broad band within the blue spectral range, with an absorption maximum of about 472 nm and 430 nm, respectively. The patent further notes that depending on the color of the material, the polymerization reaction requires light having an intensity of at least 1 to 5 mW/cm$^2$ within a very thin layer. In the practice of polymerizing tooth fillings or dental replacement parts, a light intensity of at least 250 mW/cm$^2$ is required within an appropriate period of time to achieve polymerization of sufficient degree and depth. Commercially available dental polymerization apparatuses, at least according to this '005 patent, emit light at an intensity of about 400–500 mW/cm$^2$ sometimes up to 700 mW/cm$^2$. The solid state radiation emitter according to the '005 patent is preferably a laser diode which emits a forward beam used for the polymerization proper and a backward beam used as a reference beam for controlling the intensity of the polymerization beam.

WIPO Publication No. WO 99/35995 (essentially same as U.S. Pat. No. 6,200,134) of Kovac et al. discloses a curing device for curing light sensitive compounds. The device includes generally a housing and an array of solid state light emitting diodes for having wavelengths in the range of 400–500 nm. Preferably, a peak wavelength of 470 nm is generated. The device further comprises an optical fiber light pipe for capturing the light and transmitting a beam of the light to the dental or other work surface containing a light curable compound. An optical lens may be used for focusing the light into the light pipe. It is noted on page 8 of this publication that 200–500 LEDs are used for creating the necessary light power needed for curing available dental compounds. In one embodiment of the device described, 96 LEDs are used whereas in a prototype e.g., an embodiment was made wherein 9 LEDs were utilized. See page 14. It is further noted in the publication that LEDs which include integral lenses may be employed. It should be noted that the LEDs according to this publication are generally arranged in a planar array. See, e.g., FIG. 3A. The discussion on page 20 and following notes that radiated power levels of approximately 200 mW/cm$^2$ or greater are generally necessary for curing the available dental compounds. Other intensities may be necessary for curing other light sensitive compounds. Thus the description in the WIPO publication is generally directed to fairly high power levels.

U.S. Pat. No. 5,885,082 to Levy discloses the use of laser radiation having a selected wavelength and being in the form of pulses for cutting bone and performing dental procedures. There is disclosed in Column 4, lines 27 and following a filling material for teeth constituted by a mixture formed from a liquid component composed of phosphoric acid and water and a powder component composed of a ceramic and hydroxyapatite, with the ingredients mixed in a proportion to form a paste having a consistency such that the paste is workable and sufficiently self supporting to be applied to the opening with a spatula and remain in place. The '082 patent does not involve a photocuring process and the material is not a dental polymer composite. The high peak power of the laser is believed only used for cutting and possibly hardening of the cement due to heat.

BRIEF SUMMARY OF THE INVENTION

Very generally, there is provided in accordance with the present invention a device for curing dental compositions and curing methods that comprise exposing the dental composition to be hardened to radiation from an axial array of light emitting diodes ("LEDs") having output wavelengths selected to photo-activate a hardening chemical reaction within the target composition.

The inventors have surprisingly discovered that relatively low power radiation from LEDs provides the same depth of cure as achieved by a conventional blue-light filtered dental gun, even though the LED irradiation intensity is between about 50% to 80% lower for the same exposure time. In particular, to achieve a 3.0 mm (1.5 mm ISO) depth of cure with a 60 second exposure time, an energy density of about 25 mW/cm$^2$ at the target composition is required for an LED-based dental gun vs. an energy density of about 53 mW/cm$^2$ required for a conventional blue-light dental gun. Remarkably, in the instance of a 4.0 mm (2 mm ISO) depth of cure with a 60 second exposure, an irradiation intensity of about only 38 mW/cm$^2$ at the target composition is required for a single LED-based dental gun vs. about 200 mW/cm$^2$ required for a conventional blue-light dental gun. Here the depth of cure is reported as the height of the cured cylinder. The ISO method reports the depth of cure as half the height of the cured cylinder and is sometimes given in parentheses as above and below.

Even more unexpectedly, it has been discovered that the amount of shrinkage that occurs during the curing process for irradiation intensities yielding a 3.0 mm (1.5 mm ISO) depth of cure in 60 seconds is about 7% lower when a single-LED-based dental gun is employed instead of a conventional blue light dental gun. In addition, the smaller size of an LED permits a smaller dental gun to be employed so that the level of discomfort experienced by a patient is decreased. Even further, for irradiation intensities yielding a 3.0 mm (1.5 mm ISO) depth of cure in 60 seconds, the degree of heating has been measured and found to be about 9% less when the LED-based dental gun of the present invention is employed instead of a conventional blue light dental gun. Thus the use of the present invention causes a lower thermal discomfort to the patient.

For depths of cure higher than 4.0 mm (2 mm ISO) the inventors have find surprisingly good curing characteristics with an LED gun using four LEDs. In particular, to achieve a 4.5 mm (2.25 mm ISO) depth of cure under a 40 second exposure, an energy density of about 180 mW/cm$^2$ at the target composition is required for the four-LED gun vs. an energy density of about 450 mW/cm$^2$ required for a conventional blue-light dental gun. Remarkably, for these intensities, a 40 second exposure results in a temperature rise that is up to 50% lower in the case of the four LED device as compared to the conventional blue-light dental gun. The amount of shrinkage is about 10% lower than that resulting from curing using a conventional dental and the top and bottom surface hardness obtained using the four-LED device is at least as good as that obtained with a conventional lamp.

Exemplary LEDs useful in practicing the present invention include Panasonic's "LED Blue Clear" 1500 millicandela T1-¾, LNG992CFBW and similar devices commercially available from Hewlett Packard, Toshiba and Nichia. Such LEDs emit radiation in the range from about 440 to about 500 nanometers with a power output of about 1500 millicandela. A programmable power supply 24 employed in conjunction with the above identified Panasonic LED is well know in the industry; specifically a model PS 281 produced by Tektronix may be used to obtain the results described below. It has also been discovered that LED's may be operated relatively close or at their maximum luminous output. For the Nichia LEDs with model number NSPB500S-XF3 the maximum continuous current specification is 30 milliamperes with recommended value at 20 milliamperes. Pulsed operation with a maximum current at 100 milliamperes is recommended only for a maximum duty cycle of 10%. At these operating conditions LEDs typically have lifetimes of over 50 thousand hours. However in our tests, a Nichia NSPB500S-XF3 was kept "on" for about 10 days continuously at a current of 90 milliamperes with no deterioration in its output. For dental curing applications, the LED stays on only for about 60 seconds at a time and therefore this higher current is not expected to alter the LED output characteristics for a lifetime that is comparable to the typical lifetime at recommended operating conditions.

Specific exemplary compositions may include: TPH Spectrum composite (shade A3.5) from Dentsply International, Inc. wherein the resin matrix of the composite consists of a BisGMA-adduct (adduct of 2,2-Bis[4-2-hydroxy-3-methacryloyloxpropoxy)-phenyl]propane with hexamethylene diisocyanate), ethoxylated Bisphenol-A-dimethacrylate (Bis-EMA, 2,2-Bis[4-(2-methacryloyloxyethoxy)-phenyl]propane) and triethylene glycol dimethacrylate. The combination of barium alumino boro silicate glass filler with a mean particle size below 1 μm and colloidal silica (particle size of about 0.04 μm) results in a hybrid composite with good strength and wear resistance for posterior use, combined with high surface luster and smoothness, which is an essential property for anterior use of a composite; as well as adhesives including light cure resin bond from Reliance which includes Bis-GMA and ethoxylated derivative, Polyethylene glycol dimethacrylate amine, Ketone photoinitiator. Filler particles include 60–99% fused silica and 7–13% amorphous silica. U.S. Pat. No. 5,711,665 suggests the use of a single-LED for bonding of orthodontic brackets to the tooth surface. However the use of a single LED here is to provide a 'tack' bond that temporarily secures the orthodontic bracket to the tooth. "Subsequently, remaining portions of the adhesive between the bracket base and the tooth are cured by another curing light assembly, possibly emitting a greater intensity of light can be used." This indicates that the single LED curing in this patent is intended more for temporarily forming a "tack" bond rather than completely curing the adhesive. Therefore complete curing of adhesives is also within the scope of the present invention. Surprisingly our tests with the four LED device yields a depth of cure of several mm (typically 4 mm (2 mm ISO) or more) in the adhesives with a 40–60 second exposure, far more than the cure depth that is typically required for the adhesive layer.

There is provided in accordance with the present invention a device for curing a photosensitive dental composition curable by way of irradiation with light of predetermined wavelength including as components:

(a) a power supply; and (b) a radiation source coupled to the power supply and powered thereby, the radiation source having a radiation output and including an axial array of light emitting diodes, wherein the axial array of light emitting diodes has a plurality of light emitting diodes mounted about an assembly axis defined thereby at a plurality of axial distances from the radiation output of the radiation source and being further characterized in that the plurality of light emitting diodes are directed along a plurality of divergent paths such that a position insensitive optical field is generated for curing the dental composition In a preferred device, the plurality of light emitting diodes comprises 4 light emitting diodes with a first pair of light emitting diodes mounted a first distance from the radiation output of the radiation source and a second pair of light emitting diodes mounted a second distance from the radiation output of the radiation source, the second distance being greater than said first distance. The second distance may be greater than said first distance by from about 0.5 mm to about 2 mm; typically the second distance is greater than the first distance by about 1 mm.

Each of said light emitting diodes is usually mounted about the assembly axis at an angle of from about 10° to about 30°; typically at an angle of about 20°. The device may include a lens, the outer surface of which lens defines the radiation output of the radiation source. The lens may be an aspherical lens. So, also, each of the light emitting diodes may have a characteristic maximum luminous power output and the power supply may be adapted to operate each of said light emitting diodes at a luminous power output of at least about 85 percent of its maximum luminous power output.

The position insensitive optical field is generally uniform over an axial distance of from about 1 to about 5 mm from said radiation output of said radiation source.

In another aspect of the present invention there is provided a method of curing a photosensitive dental composition curable by way of irradiation with light of predetermined wavelength by way of:

A. applying the said photosensitive dental composition to a dental surface, or a cavity; and B. irradiating the dental composition with a position insensitive optical field generated by way of an irradiation source including an axial array of light emitting diodes, wherein the axial array of light emitting diodes comprises a plurality of light emitting diodes mounted about an assembly axis defined thereby at a plurality of axial distances from the radiation output of the radiation source and being further characterized in that the plurality of light emitting diodes are directed along a plurality of divergent paths.

Still further aspects and advantages of the present invention will become readily apparent from the discussion which follows.

BRIEF DESCRIPTION OF THE DRAWINGS

The invention is described in detail below with reference to the various figures wherein like numerals designate similar parts and wherein:

FIG. 6 is a plot of typical LED current vs. LED luminous power output for LED's useful in connection with devices and processes of the present invention;

DETAILED DESCRIPTION

Figure 1:
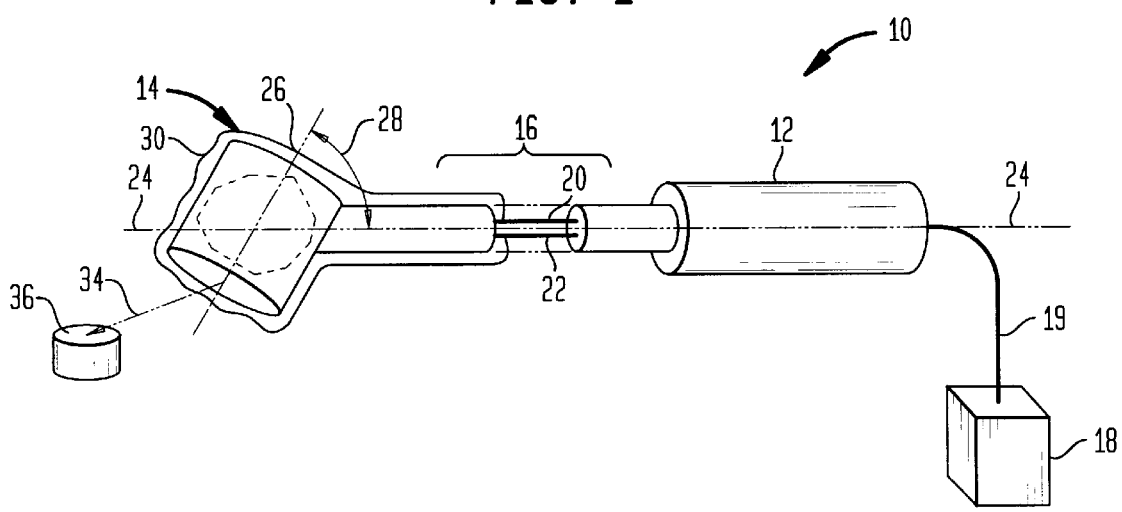
FIG. 1 is a schematic view in perspective showing generally the configuration of a compact, hand held photocuring device of preferred class of the present invention.

In order to demonstrate the improved dental curing obtained using LED radiation, comparative tests were completed using an LED dental curing apparatus of the class described generally herein and a conventional dental radiation curing unit like that available from Dentsply International Inc., Caulk Division, Milford, Del., specifically the Spectrum™ Curing Unit, Model 200R. This unit is typical of other commercially available conventional curing units and employs a quartz halogen lamp filtered with a blue filter and includes an on-board radiometer to assure minimum levels of output power. The Model 200R provides a minimum operating intensity of about 450 mW/cm$^2$ in the 400–500 nanometer wavelength range at the output of its light guide. This intensity decreases as distance to the target from the output end is increased.

The initial tests described herein were completed using commercially available dental compositions; in particular, two different products, the DenMat® Marathon V #5474 and the Caulk TPH Spectrum Shade A 3.5 compositions were used to obtain comparative performance data between the LED curing method of the present invention and prior art conventional methods. In the following illustrative tests, two comparisons are made. In the first comparison the single-LED and dental curing apparatus was operated at an energy output level of about 25 mW/cm² at the dental composition target 36 and was stationed at a distance of about 7 mm±2 mm above the target 36 for a period of 60 seconds. The curing performance of this source is compared to that obtained using both the four-LED dental curing apparatus and the conventional Spectrum™ 200R Curing Unit applying energy levels of 25 mW/cm² and 53 mW/cm², respectively, at the target 36 for a period of 60 seconds. In the second comparison a four-LED dental curing apparatus operated at an about 180 mW/cm² is compared to a conventional curing unit at about 450 mW/cm² for a period of 40 seconds. Variation of light intensity of the conventional curing unit for these tests was achieved through the use of neutral density filters and/or by varying the distance between the output end and the target composition. In all instances the actual intensity was determined at the location of the target composition using a variable area aperture followed by an optical power meter to record the optical power incident on the aperture. Unless otherwise indicated, all irradiation intensities reported below refer to the energy applied at the irradiated surface of the dental composition target 36.

(1) Measurement of Depth of Cure

Depth of cure was measured in accordance with the established industry standard depth of cure measurement technique defined by the International Organization for Standardization as ISO DIS 4049; 1998. This technique employs a 7.0 mm thick stainless steel mold having a 4.0 mm diameter cylinder that extends through the mold. The thickness of the mold is 2 mm greater than twice the maximum depth of cure claimed. The dental composition to be cured, in this instance, the Caulk TPH Spectrum Shade A 3.5 composition, is tightly filled into the cylinder and the open ends of the cylinder are covered with a polyester film. One end of the cylinder is irradiated with curing radiation under test conditions and then the uncured material is removed from the cylinder. The cured cylinder is removed from the mold and the cured height is measured with a micrometer. The ISO depth of cure is recorded as half the height of the cured cylinder and the test is repeated twice. As described above, both radiation sources, the dental curing apparatus 10 and the Spectrum™ 200R Curing Unit were used to cure the cylinder of dental composition.

Depth of cure for a 4 mm diameter cylinder mold for a 60 second exposure was then measured and determined to be 3.0±0.2 mm (1.5±0.1 mm ISO depth of cure) for the single-LED radiation and the four-LED curing apparatuses 10 operated at an irradiation intensity of 25 mW/cm². In contrast, to obtain a similar depth of cure using conventional blue-light radiation like that emitted from the conventional Spectrum™ 200R Curing Unit, it was necessary to operate at an irradiation intensity of 53 mW/cm². In the instance of obtaining a 4.0 mm depth of cure (2.0 mm ISO depth of cure) with a 60 second exposure, the single-LED and the four-LED radiation curing apparatuses were operated at 38 mW/cm² and 50 mW/cm², respectively, and the conventional blue-light radiation-curing gun was operated at about 200 mW/cm². To achieve a 4.5 mm depth of cure (2.3 mm ISO depth) under a 40 second exposure using a four LED head, an irradiation intensity of about 180 mW/cm² at the target composition 36 is required for the LED-based dental gun vs. an irradiation intensity of about 450 mW/cm² required for a conventional blue-light dental gun. Thus, the single-LED and the four-LED curing apparatus may be operated at a much lower irradiation intensity than conventional dental guns to obtain an essentially equivalent or greater depth of cure.

(2) Measurement of Shrinkage

The degree of shrinkage associated with polymerization with a polymer dental composition was measured in accordance with an established ADAHF industry standard technique using a dilatometer. A dab of dental composition with approximately 0.1 gram mass is placed on a standard microscope slide that has been tared on a 4-digit balance. The composition is spread on the slide with a spatula, keeping the composition less than 1.5 mm thick and less than 5 mm in diameter to assure complete curing. The weight of the composition is recorded to 4 decimals. An open glass measurement tube having a cup-shaped end section is positioned with the cup-shaped end section facing upwards and the microscope slide with the dental composition is inverted over the cup so that the composition is centered in the cup. The slide is clamped secured to the measurement tube with a clamp, rotated 180-degrees to the desired orientation and filled with mercury. A linear displacement transducer, a Lucas Shaevitz LVDT, assembly is slowly lowered into the tube until it rests on top of the glass measurement tube with its plunger floating on the mercury. A thermistor (an Omega 44133 thermistor) is built into the cup-shaped section of the measurement tube and positioned to be in contact with the mercury surrounding the composition being tested. The LVDT assembly and the thermistor are connected to a control box (not shown) and interfaced to a computer (not shown). Both radiation sources, the single-LED dental curing apparatus and the conventional Spectrum™ 200R Curing Unit were used to irradiate the dental composition for 60 seconds at output power levels of that yield 25 mW/cm² and 53 mW/cm², respectively. In addition, for a 40 s exposure, the 4-LED dental curing apparatus operated at about 180 mW/cm² is compared to the conventional curing unit operated at about 450 mW/cm².

A software program developed by the ADAHF residing within the computer is used to acquire and analyze data related to an expansion of the mercury from the LVDT and mercury temperature changes registered by the thermistor. The change in mercury level results from two sources: (1) shrinkage in dental composition due to polymerization, and (2) expansion in mercury due to irradiation induced heating. The software program calculates the expansion in mercury from the thermistor temperature data. The overall volume change is calculated based on LVDT data. From the combination of these data, the shrinkage within the dental composition may be calculated once the final density of cured polymer is provided. Final density of the polymer is measured using a Mettler Toledo AT 261 balance in combination with a Mettler Toledo 210485 density determination kit.

(3) Measurement of Heat

The increase in temperature associated with a 60-second exposure for achieving a depth of cure of 3.0 mm (1.5 mm ISO depth of cure) was measured using the ADAHF dilatometer described above. Again, the dental curing apparatus and the conventional Spectrum™ 200R Curing Unit were used to expose dental composition target for 60 seconds at irradiation intensities measured to be 25 mW/cm² for the single-LED and the four-LED curing apparatus and 53 mW/cm² in the case of the conventional blue-light dental gun. In addition, temperature rise was compared for a 40 second exposure from a four-LED curing apparatus operated at about 180 mW/cm² to a conventional curing apparatus operated at about 450 mW/cm².

The dental curing apparatus using an LED produced an initial temperature increase of about 0.8° C. whereas in contrast the conventional light Spectrum™ 200R Curing Unit produced an initial temperature increase of about 0.9° C. Thus the single-LED dental curing apparatus 10 produced lower overall heating of the composition in contrast to the higher overall heating from the conventional blue light curing unit. Thereby, when treated with the dental curing method of the present invention, a patient will experience a significantly lower degree of discomfort as a result of the about 8% lower temperatures during curing of an embedded dental composition with a single-LED device. A 40 second exposure of radiation from the four-LED device at about 180 mW/cm$^2$ yields a temperature rise of up to 50% lower than the conventional curing unit operated at about 450 mW/cm$^2$.

Shrinkage measurements made using these same irradiation intensities, which yield a 3.0 mm depth of cure (1.5 mm ISO depth of cure), showed that the single-LED dental curing apparatus of the class of the present invention operating at 25 mw/cm$^2$ produced a shrinkage of 2.8% whereas in contrast the conventional Spectrum™ 200R Curing Unit operating at 53 mW/cm$^2$ produced a shrinkage of about 3.0%. A 40 second exposure of radiation from the four-LED device at about 180 mW/cm$^2$ yields about 2.2% shrinkage in the composite, while the conventional curing unit operated at about 450 mW/cm$^2$ yields a shrinkage of 2.5%.

(4) Measurement of Hardness:

Hardness measurements were performed on a dental composition cured with a convention curing lamp and the four-LED device using a standard hardness tester (Barber-Coleman Impressor Model No. GYZJ 934-1). The composition was slightly over-filled into a stainless steel mold with a diameter of 5 mm and a thickness of 2 mm. The two open ends of the mold were covered with polyester film and the mold was pressed between two glass plates to firmly pack the composite in the mold. The mold was irradiated for 20 seconds using three comparative sources: A conventional curing unit operated at about 450 mW/cm$^2$ was compared to a four-LED apparatus operated at about 180 mW/cm$^2$. The composition used was the Heliomolar Radiopaque® Shade A3. For both these sources the top surface hardness is about 60 while the bottom surface hardness is measured to be about 53 on the Barber-Coleman hardness scale.

(5) Failure Mode

Although actual results were not experimentally determined, it is well known within the industry that dental curing guns employing conventional radiation sources gradually lose power output during the life of the dental gun. For example, a negative correlation between the depth of cure and the age of light-curing guns has been reported, with older Heliotests (Ivoclar-Vivadent) units tending to cure a Z100 Composite (3M) dental composition to less depth than newer units [Prim Dent Care Sep. 4, 1997 (3): 91–4]. Because of this time loss of power output, curing lights are considered as unsuitable for use with a reading of less than 200 mw/cm$^2$ using a curing radiometer and greater than 50 mw/cm$^2$ using a heat radiometer [J Dent Mar. 27, 1999 (3): 235–41] underscoring the necessity of monitoring the output of conventional dental curing guns as they age in use. In contrast, an inherent characteristic of LED radiation sources like those used in the present invention is a stable level of output radiation during the operating life of a LED, with a catastrophic failure that is readily noticeable by an operator whenever the output declines.

(6) Relative Costs

The expenses associated with conventional radiation dental curing guns comes about as a result of the need to provide relatively high output power with appropriate filtering and cooling means. Such guns and the associated power supply cost in the $600–1,000 range. In contrast, the LED-base dental curing method of the present invention employs low power LEDs costing in the $5 range per LED ($20 for a four-LED head) and not requiring the high output power, filtering and cooling means of conventional dental curing guns.

The following Table 1 contains the results of preliminary testing in a condensed form. The advantages of using LED curing are evident.

TABLE 1

Comparison of Curing Performance

|  | New LED Prototype with: | | Conventional |
| --- | --- | --- | --- |
| Radiation Source | Single LED Head | Four LED Head | Curing Lamp |
| Power density at the target composition (Caulk TPH Spectrum Shade A3.5) that achieves a cure depth [1] of: | [2] | [2] |  |
| 3.0 mm (60-s exposure) | 25 mW/cm$^2$ | 25 mW/cm$^2$ | 53 mW/cm$^2$ |
| 4.0 mm (60-s exposure) | 38 mW/cm$^2$ | 50 mW/cm$^2$ | 200 mW/cm$^2$ |
| 4.5 mm (40-s exposure) | 38 mW/cm$^2$ (3.7 mm) [3] | 180 mW/cm$^2$ | 450 mW/cm$^2$ |
| Temperature rise in target composition (Caulk TPH Spectrum Shade A3.5) for irradiation that achieves a cure depth of: |  |  |  |
| 3.0 mm (60-s exposure) | 0.8° C. | 0.8° C. | 0.9° C. |
| 4.5 mm (40-s exposure) | 0.8° C. (3.7 mm) [3] | 1.0° C. | 1.8° C. |
| Shrinkage in composite (Caulk TPH Spectrum Shade A3.5) for irradiation that achieves a cure depth of: | [9] | [9] | [9] |
| 3.0 mm (60-s exposure) | 2.8% | 2.9% | 3.0% |
| 4.5 mm (40-s exposure) | [8] (3.7 mm) [3] | 2.2% | 2.5% |
| Beam Divergence | ~6 degrees | Negligible [4] | ~27 degrees |

TABLE 1-continued

Comparison of Curing Performance

|  | New LED Prototype with: | | Conventional |
| --- | --- | --- | --- |
| Radiation Source | Single LED Head | Four LED Head | Curing Lamp |
| Relative Cost of Light Source | ~$5 | ~$20 | ~$100 |
| Minimum cure time for Heliomolar Shade A3 [5] | NA | 23 s | 25 s |
| Depth of cure/Top surface hardness achieved with a 40 s exposure at optimum operating power [6]: | | [7] | |
| Caulk TPH Spectrum Shade A3.5 | 3.7 mm/63 | 5.1 mm/63 | 4.5 mm/69 |
| Kerr Prodigy Shade A3.5 | 3.0 mm/51 | 4.1 mm/55 | 4.5 mm/69 |
| Top/bottom surface hardness of a 5 mm diameter, 2 mm thick cured piece of Heliomolar shade A3 at 20 s cure time. | [8] | 60/53 | 60/53 |
| Autoclavable | Replaceable protective sheath | Replaceable protective sheath | Yes (tip) |
| Minumum life expectancy at higher currents used for this application (estimated number of 60-second curing operations) | >40,000 | >40,000 | Typically quoted in the few thousands [10] |
| Degradation with time | None until catastrophic failure | None until catastrophic failure | Continual degradation with time |
| Radiometer Requirement | NO | NO | YES |

[1]- Cure depth is defined as the height of the cured cylinder of composite resin. To obtain depth of cure as defined in the ISO method, this height needs to be divided by two.
[2]- It was shown by Pradhan, Melikechi and Eichmiller in the Journal Dental Materials that the cure depth is higher when the spectral emission profile of the source matches the spectral absorption peak of the photo-initiator in dental composite resins. This being the case, the LED based devices can match the curing performance of the conventional curing lamp at a much lower irradiation power density.
[3]- A Single-LED head operated under optimum operating conditions yields a cure depth of 3.7 mm with a power density of ~38 mW/cm$^2$. Higher depth of cure requires the use of the Four-LED Head.
[4]- The unique Four LED geometry achieves uniform intensity over a distance of 5 mm from the head and this amounts to negligible beam divergence over the operating distance.
[5]- Minimum curing time is defined as the time required to achieve a hardness magnitude at the bottom surface of a 2 mm thick cured piece that is within 90% of the hardness magnitude at the top surface.
[6]- 38 mW/cm$^2$ for the Single-LED Head, 230 mW/cm$^2$ for the Four-LED head and 450 mW/cm$^2$ for the conventional curing lamp.
[7]- Hardness in Barber-Coleman Hardness Scale. For comparison, typical readings of Aluminum alloys range from a minimum of 35 to a maximum of 85 on the Barber Coleman scale.
[8]- The single-LED head is not suitable for deep curing. A four-LED head is therefore recommended.
[9]- The estimated uncertainty on the shrinkage measurements is ±8% of the reported shrinkage, which is close to ±0.2%.
[10]- Plasma ark sources probably have a lifetime that is comparable to the LEDs but they require several hundreds of dollars to replace.
NA- Not applicable It is to be understood that the specific embodiments of the invention described herein are illustrative of the principles of the invention and that other modifications may be employed which are still within the spirit and scope of the invention. For example, in one alternate exemplary embodiment, a dental composition having a different formulation from those noted above may be employed. It is known from the literature that Axis and Thermoresin LC II dental compositions may be cured with both UV and visible radiation while another composition Dentacolor is cured substantially by visible light [J Oral Rehabil Oct. 25, 1998 (10): 770–5]. To confirm the effectiveness of LED curing, the depth of cure of a second commercially available dental composition known as Marathon V available from Den-Mat® was also evaluated using an LED-based curing method in the aforedescribed ISO DIS 4049 testing method. The test results were essentially a duplicate of those reported in the above. It was shown that the single-LED method provides a relatively constant depth of cure as long as the LED is positioned within a distance of 8 mm from the dental composition, a result of the low divergence of the LED beam in comparison to the highly divergent radiation generated within a conventional filtered light dental gun. Optimum distance from the dental composition target is seen to be in the range of 1–8 mm for the single-LED curing devices and methods described herein. The unique geometry of the four-LED device provides optimum performance at a distance of 1–5 mm from the dental composition target.

In another embodiment, a light emitting diode having other than "clear blue" wavelengths may be employed as long as the dental composition may be cured by the application of corresponding radiation. It is known from the literature that microfilled and hybrid composition materials designed for prosthetic veneer may be cured with different types of light, in particular both xenon light and metal halide light sources. Depending on the choice of light source and the choice of dental composition, an increased exposure duration increases the depth of cure for all combinations [J Oral Rehabil May 25, 1998 (5): 348–52]. Accordingly the present invention may be practiced using any LED having its wavelength selected to provide radiation energy in the effective curing range for the composition being employed. In this alternate exemplary embodiment, the duration of radiation exposure with a LED as disclosed in the present application may be increased to accomplish a minimum acceptable depth of cure, depending on the selection of LED radiation wavelength and the selection of dental composition.

Figure 2:
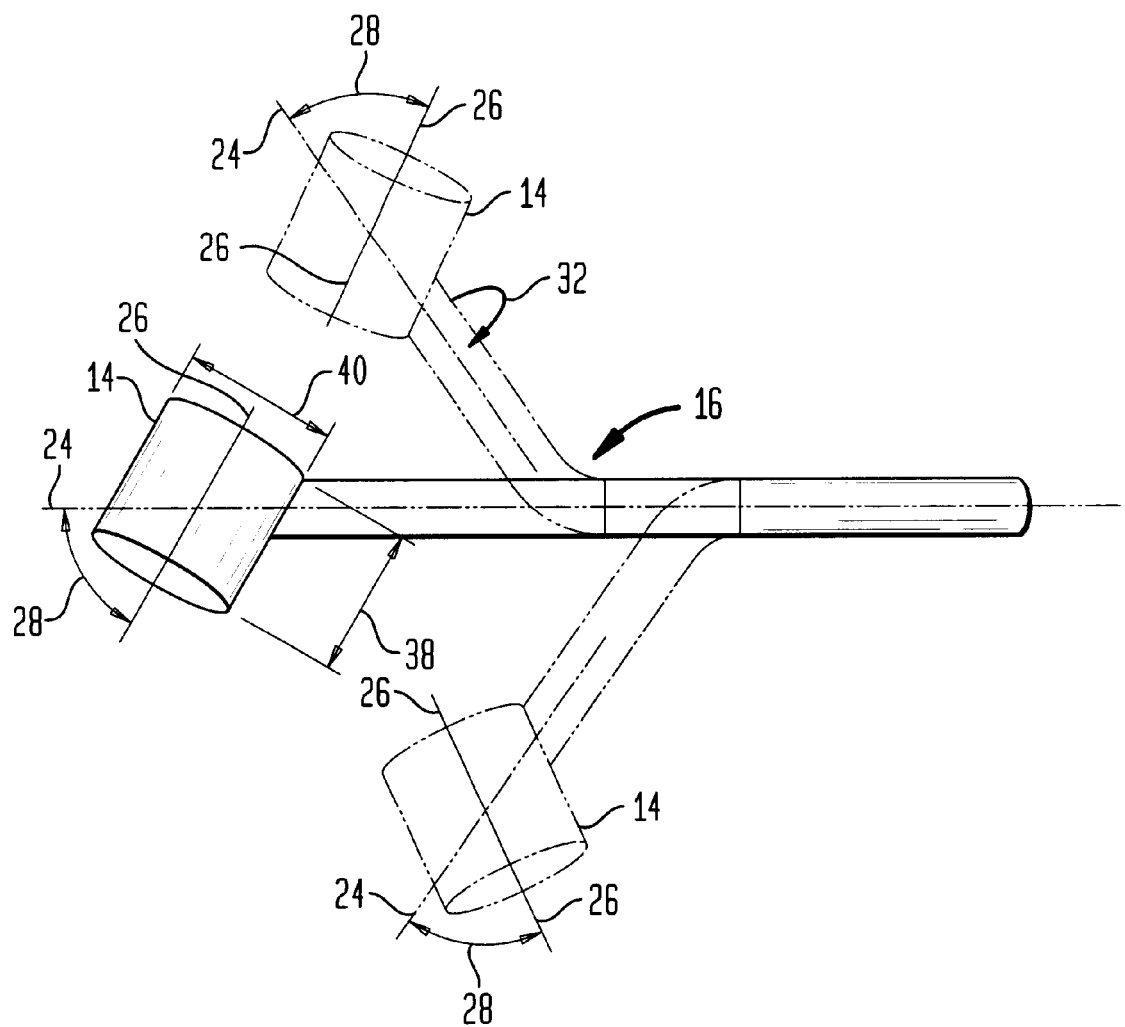
FIG. 2 is a schematic view of the device of FIG. 1 provided with a flexible arm illustrating bending and rotation of the LED head assembly of the device.

Referring to FIGS. 1 and 2 there is provided a hand held curing device 10 which includes a handle 12 adapted for gripping by a user as well as a compact LED mounting head assembly 14 attached to the handle by way of a flexible arm 16. Arm 16 may be of the "gooseneck" type, made up of a plurality of annular segments such that it can rotate or bend to a temporarily fixed position.

There is further provided a power supply 18, which typically includes a transformer, connected to the mounting head assembly by way of a power cord 19 including wires 20, 22 in order to power the LEDs mounted herein. Power cord 19 is preferably of the retractable type as is well known. Alternatively, the device may be battery powered as is also known in the art.

In FIG. 1, arm 16 is in a coaxial configuration with handle 10, that is, both arm 16 and handle 12 are aligned along a device axis 24 in a straight line. In a preferred embodiment, a head assembly mounting axis 26 has a head assembly mounting angle 28 between axes 24, 26 of from about 40° to about 80° and preferably about 60° as is shown in the Figures. There is optionally provided a removable sheath 30 to cover the device, which may be changed between uses of the device and prevent cross contamination between patients. Sheath 30 is generally constructed of polymer film.

It is shown in FIG. 2 that the compact LED mounting head assembly may be suitably positioned by bending, wherein axis 24 becomes bent, or rotating about axis 24 as indicated by arrow 32. The inventive device also provides for adjusting the direction of the output path of radiation indicated generally at 34 by way of a lens or the position of the LEDs within compact head 14 as further discussed herein. The foregoing combination of features makes the device readily adjustable so that it may be used to irradiate a target composition indicated at 36 in a fully optimized manner.

Likewise, an important feature of device 10 is the compact size of head assembly 14. In accordance with the invention, head 14 may have a height 38 of 10–20 mm, preferably about 15 mm and a diameter 40 also of about 10–20 mm, preferably about 15 mm.

Figure 3A:
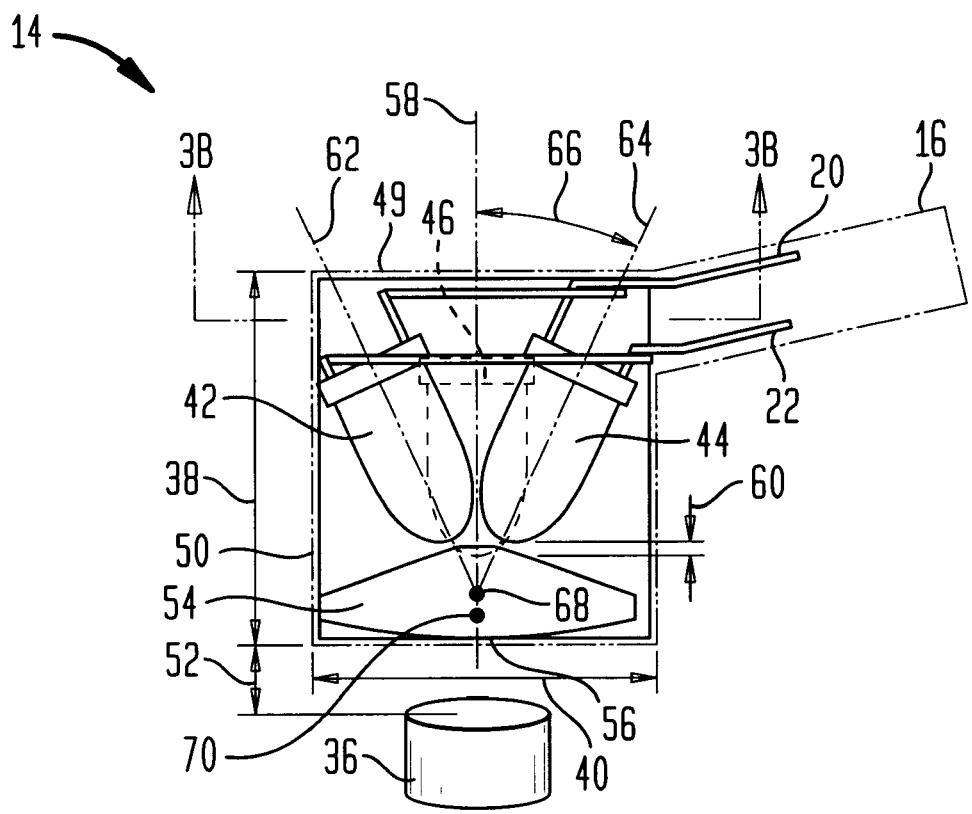
FIGS. 3A and 3B are schematic views in section and in elevation (3A) and in section and plan (3B) showing the geometry of a 4-LED head assembly arranged in an axial array about a symmetry axis, which may be affixed to the device of FIG. 1.
Figure 3B:
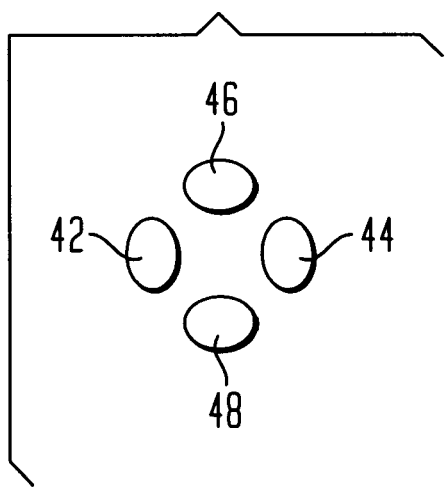

FIGS. 3A and 3B illustrate a four LED compact mounting head assembly 14 useful for mounting on device 10. FIG. 3A is a schematic view along the centerplane of assembly 14 showing three LEDs, 42–46, whereas FIG. 3b is a top plan partial schematic view of the assembly 14 of FIG. 3a, showing all four LEDs 42–48. Compact mounting head assembly 14 includes a top 49 and a sidewall 50 and is configured for housing and optionally mounting LEDs 42–48 which communicate with the power supply via wires 20, 22 through arm 16. The LEDs are mounted such that the LEDs may be suitably positioned with respect to a target composition indicated at 36 at a distance 52 from the output of LED head assembly 14. Distance 52 is suitably from about 1–8 mm and preferably about 4 mm. The LED heads shown in FIGS. 3A through 4B generate an optical field that is relatively position insensitive and optimal curing results can be achieved over a variety of distances, as further discussed below.

Head assembly 14 of FIGS. 3A and 3B includes a single convergent lens 54 which may be an aspheric lens. In the device shown, distance 52 is measured from the center of outer surface 56 to target composition 36. LEDs 42–48 are arranged in an axial array about an axis of symmetry 58 wherein LEDs 46, 48 are mounted directly on lens 54 and LEDs 42, 44 elevated above lens 54 a distance 60 and are thus further from the output of the head assembly 14 (in the case shown in FIGS. 3A and 3B outer surface 56 of lens 54) by that amount. In other words, LEDs 46 and 48 are mounted at a first distance form the output of the device and LEDs 42, 44 are mounted a second distance, greater than the first distance from the output of the device; the difference being distance 60. Distance 60 is generally from about 0.5 mm to about 2 mm with about 1 mm being typical.

Each LED has an axis such as axes 62, 64 of LEDs 42, 44 which make an angle 66 with assembly axis of symmetry 58 as shown. Angle 66 may vary between LEDs and is typically between about 10° to 30° with about 20° being preferred.

Thus, arranged in an axial array, LEDs 42–46 define a plurality of divergent radiation paths thereby generating a position insensitive optical field for curing composition 36. As used herein, the terminology "a plurality of divergent radiation paths" means and includes arrangements where all of the LED are not directed to a single common focal point; whereas the terminology "axial array" refers to the fact that at least two LEDs are located at different distances from the output. In the embodiment shown in FIGS. 3A and 3B LEDs 42, 44 are angled such that their outputs (along axes 62, 64) are directed at common focal point 68 whereas LEDs 46, 48 are directed to focal point 70. In yet other embodiments the LEDs are arranged about an assembly axis such that there are no focal points common to any two LEDs.

Figure 4A:
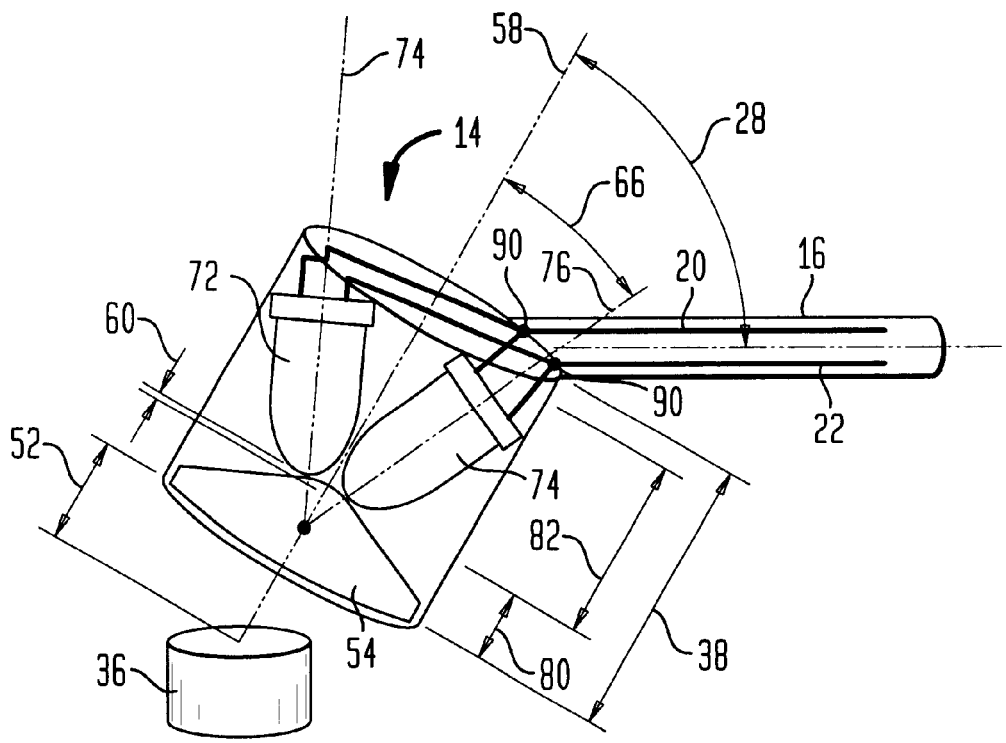
FIG. 4A is a schematic view of a LED head assembly similar to the type shown in FIGS. 3A and 3B.
Figure 4B:
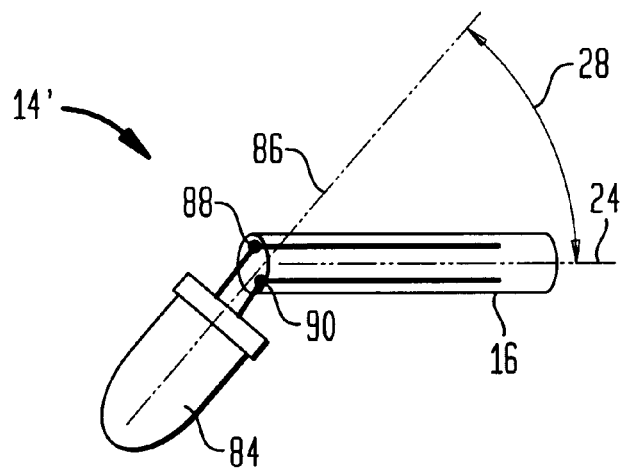
FIG. 4B is a schematic diagram showing a portion of an LED head assembly having a single LED.

FIG. 4A is an alternate embodiment of the arrangement of FIGS. 3A and 3B wherein adjacent LEDs 72, 74 touch the lens and two rearward LEDs (not shown) are elevated a distance 60 of 1 mm. Here again, head mounting angle 28 is suitably 60° and the angle 66 between assembly axis 58 and the axes 74, 76 of LEDs 72, 74 is 20°. The compact dimensions of device 10 are further appreciated from FIG. 4A. Lens 54 has a thickness 80, for example, of about 5 mm at its thickest point whereas the inclined LEDs have a height 82 of about 8.5 mm. The overall height 38 of the LED head assembly is thus 15 mm or less. In a single LED embodiment shown in part in FIG. 4B, a single LED 84 replaces the axial array of LEDs shown in the various Figures. Single LED 84 has an axis 86 which preferably makes an angle 28 of about 60 degrees with axis 24 of device 10. A single LED head assembly 14' may be employed when it is desired to minimize the overall dimension of head 14. Thus, head assembly 14' may be made interchangeable with four LED head assembly 14 such that either LED head assembly may be releasably connected to arm 16 by way of plug means indicated at 88, 90 whereby the head assemblies are mechanically and electrically coupled to arm 16 and thus handle 12.

Figure 5A:
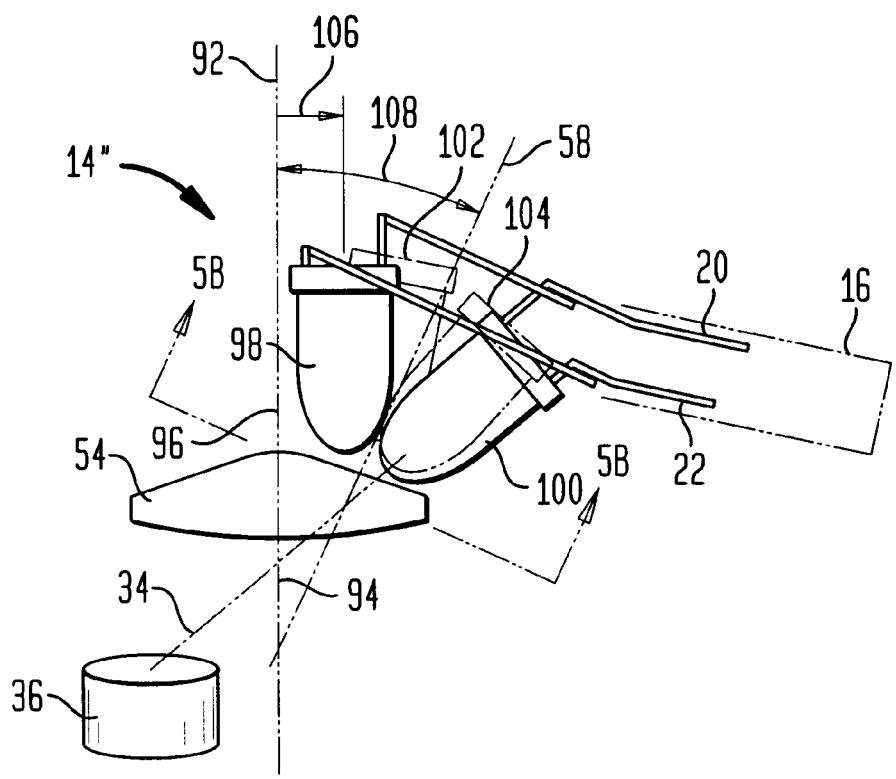
FIGS. 5A and 5B are partial schematic views in section and elevation (5A) and in section and plan (5B) showing the geometry of a four LED head assembly wherein the LEDs are axially arrayed about an axis of symmetry defined thereby.
Figure 5B:
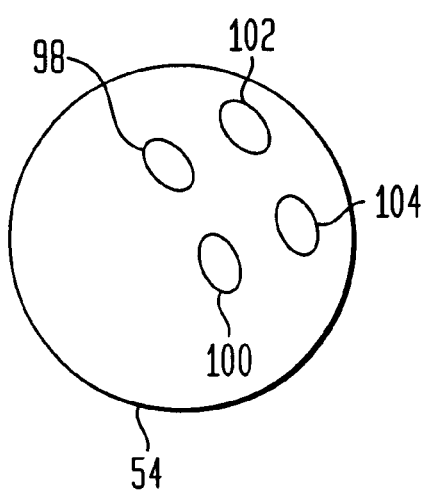

In FIGS. 5A and 5B there is shown an arrangement wherein the LEDs are mounted "off axis" of lens 54. Lens 54 has an axis 92 defined by its focii 94, 96 as shown in FIG. 5A. Lens 54 is mounted as in FIGS. 3A, 4A in a housing generally indicated at 14". LEDs 98, 100, 102 and 104 are mounted as shown in FIGS. 5A and 5B adjacent to lens 54, wherein they form an axial array about LED assembly axis 58 as described above. Here, however, axis 58 is not coincident with head assembly mounting axis 26 in the configuration shown in FIGS. 5A and 5B, where axis 92 of lens 54 may be coincident with the axis of the head generally if so desired. The axial assembly of LEDs about assembly axis 58 is laterally offset from axis 92 by a distance indicated at 106. This distance is the distance from the geometric center of the top of the LED closest to the axis of lens 54. Axis 58 is also angularly offset from axis 92 by an angle 108; typically from about 10° to about 50°. It should be appreciated that the angle from radiation emitted by LEDs 98–104 generally follows the direction of axis 58 but is refracted toward the axis of lens 54 from its outer portions. Note from FIG. 5B which is a view along the line 5B—5B of FIG. 5 and that the LEDs are concentrated on one side of the lens, on the portion of the head closer to handle 16. In this configuration, convergent lens 54 serves the dual functions of focusing the light and directing it outwardly toward a hard to reach target 36. Moreover, the path can be adjusted either by way of distance 106 or angle 108.

FIG. 6 is a characteristic plot of LED current versus luminous power output for LEDs useful in the devices of the present invention. Such devices have a characteristic maximum luminous power output 110 where increasing the current does not increase the optical power output. It has been found such devices are advantageously operated in connection with curing dental compositions at an optical power output of at least about 85% of their characteristic maximum luminous power output as indicated at 112 on FIG. 6. The preferred current operating range is shown as the shaded area on FIG. 6 which may be 90, 95 or 100 percent of the maximum luminous power output of the device.

Figure 7A:
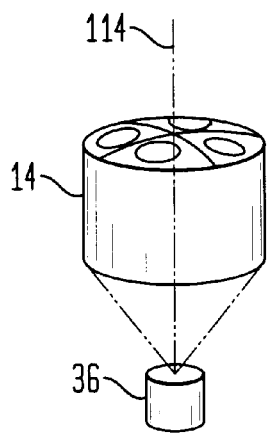
FIGS. 7A and 7B illustrate respectively the LED head assembly of FIGS. 4A and 4B disposed directly opposed to a target composition and inclined with respect to a target composition.
Figure 7B:
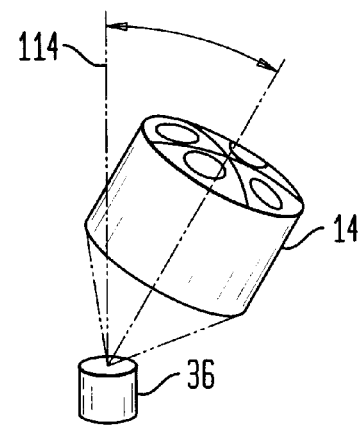
Figure 8:
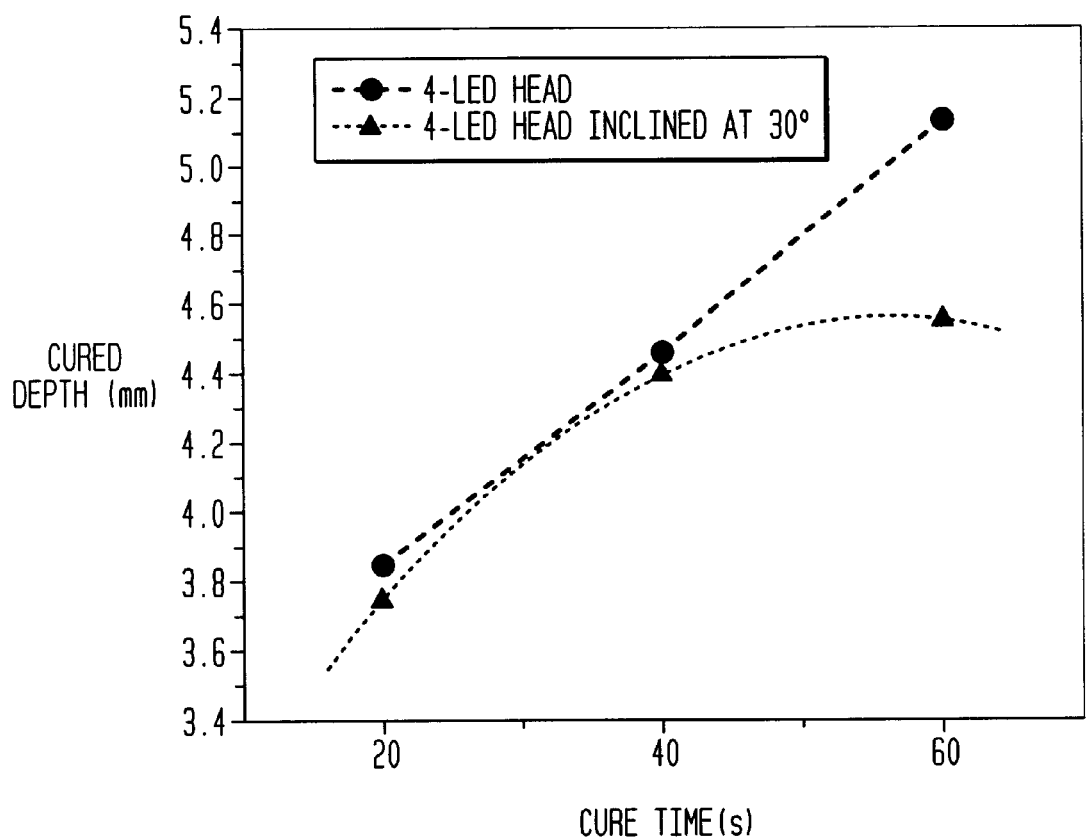
FIG. 8 is a plot of depth of cure vs. time for the LED head assembly orientations shown in FIGS. 7a and 7b.

The curing device is further appreciated by considering FIGS. 7A, 7B and FIG. 8. In FIG. 7A, a four LED head assembly 14 as described above with an axial array of LEDs is located directly above a target composition 36, wherein in FIG. 7B head 14 has been rotated 30° off of axis 114. In FIG. 8, the cure depth versus time is compared for the two orientations. There is virtually no difference in cure depth versus time until cure depths of over 4.5 mm indicating the position insensitivity of the optical field generated and the overall effectiveness of the device.

Some salient points of this invention and related inventions forming the subject matter of patent filings contemporaneous with this application is the compactness made possible by a unique combination of features. Although it is within the skill of one knowledgeable in the art to use a large number of LEDs to obtain a desired depth of cure with a specified time (e.g. 3 millimeters within 60 seconds), it is a challenge to obtain the same performance with a reduced number of LEDs. This reduction, however, is necessary to make the assembly of LEDs compact. Out work shows that the we can minimize the number of LEDs for a desired performance and gives surprisingly good results. This is achieved by doing the following in combination:

a) Driving the LEDs with a non-traditional current-In existing technologies the LEDs used are driven at a specifications provided by the LED manufacturers. The current invention operates an LED at an optimum and non-traditional operating current 70 that is well beyond the typical specifications of the manufacturer. Under these conditions, our tests surprisingly indicate no detrimental effects on the LED used in the manner indicated for the current invention. The current invention utilizes a powerful LED 34, with at least the output of an LED like the Nichia NSPB500S-XF3;

b) Novel and Unique geometry of the LED head—The novel geometry yields surprising intensity and uniformity of irradiation of the material to be cured. Our data shows excellent results in terms of the speed of cure, the depth of cure, the hardness and the uniformity of cure. The device is to be positioned at a distance of 4.0 mm from the curing site for optimal curing performance but the design surprisingly allows this optimal distance to vary anywhere from 1.0 to 5.0 mm without appreciably affecting the curing performance. This 4.0 mm allowed variation in the distance between the output end of the head and the curing site is typically the maximum variation possible with the mouth fully open.

The novel geometry consists of a combination of a minimal number of LEDs. In one preferred embodiment the combination consists of four LEDs. The axis of each LED is optimally oriented from the axis of the four-LED combination at an angle. A single lens and optimal elevation of LEDs as described above and further noted below are further unique features of the compact device.

The single aspheric lens shown in FIG. 3A and following is a novel feature in this design that efficiently collects light from the combination of LEDs and delivers maximum light intensity at the curing site. Any other conveniently shaped convergent lens such as a cylindrical lens and other custom built lenses that will efficiently collect light from any combination of LEDs for efficient curing.

Traditionally a lens is used on-axis for the purpose of focusing. Our study shows that the single lens can be used off-axis in a non-traditional manner to achieve desired results. With appropriate orientation angle and position of the LED assembly axis with respect to the axis of the lens, the direction at which light emerges from the head can be varied to reach locations in the mouth that are otherwise hard to reach (see FIG. 5A).

An elevated LED Architecture achieves axial uniformity of radiation. This feature of the device results in a surprising axial uniformity of the curing irradiation, generating a position insensitive optical field. The distance of the LED head from the curing site can waiver when the practitioner holds the device in hand. The great advantage of this feature is that the exact distance between the head and the curing site can waiver up to several millimeters without affecting the curing performance. Each LED in the LED combination can be individually elevated to a distance from the surface of the lens. In a preferred embodiment two diametrically opposite LEDs in a four-LED combination can be slightly elevated to a convenient distance from the surface of the lens. No attempt is made to focus the light from the LEDs to a single point. On the contrary, focusing at a single point is to be avoided so as to decrease the sensitivity of the curing characteristics to the exact distance between the head and the curing site. In this respect, a plurality of divergent paths of radiation are preferred Complementing the above aspects are:

Compactness—The entire LED head is contained in a head that has maximum dimensions of about 15×17 mm. This should allow convenient positioning of the head over the oral curing site. The connection between the head and the power supply can be a thin arm, which needs to carry a thin wire rated for carrying the <500 milliamperes current to the LED assembly head, can be as thin as 3–5 mm in diameter.

Transformer—for the current device, no specific attempt is being made to make it self-contained but it can be so. In one embodiment of the device there will be no rechargeable batteries. A thin cable that is long enough for dental usage will connect the handle to the power supply/transformer to provide the necessary power to the LED head. Rechargeable batteries are expected to hamper commercialization of a device embodiment due current requirements. With 4-LEDs running at the manufacturer's specifications and without the aspheric lens the light intensity is expected to be too weak to efficiently cure the dental resin. With a larger number of LEDs the current becomes a problem. Use of a transformer relaxes these constraints and allows the optimum current to be delivered to the head for as long as it is desired.

Flexible gooseneck arm—As shown in FIG. 2, the arm connecting the LED head to the handle can be as thin as 3–5 mm and can, in the preferred embodiment, be a "gooseneck" arm that can be bent and/or rotated to position the LED head at the desired orientation. The head itself can be attached to the arm at a convenient angle and can be rotated about the axis of the arm.

Flat printed circuit board—The LEDs will be held at the specified angle by direct bonding onto the lens or by an appropriate socket designed to fit inside the LED head. The device will use a flat printed circuit board.

Protective sheath—The compactness of the device allows for a protective layer or sheath of various kinds to be placed covering the head and the arm between patients to prevent cross contamination. The protective sheath could be a cap that fits directly over the head or an elastic membrane that can be stretched over the device. In one embodiment, the lens itself could be a part of a molded piece that can be disposed after each patient.

While the invention has been fully described in the context of particular embodiments, modifications to such specific embodiments within the spirit and scope of the present invention will be readily apparent to those of skill in the art. The invention is defined in the appended claims.

What is claimed is:

1. A device for curing a photosensitive dental composition curable by way of irradiation with light of predetermined wavelength comprising:
   (a) a power supply; and
   (b) a radiation source coupled to said power supply and powered thereby, said radiation, source including an axial array of light emitting diodes and having a generally planar common radiation output, wherein said axial array of light emitting diodes comprises a plurality of light emitting diodes mounted about an assembly axis defined thereby at a plurality of axial distances from said radiation output of said radiation source and being further characterized in that said plurality of light emitting diodes are directed along a plurality of divergent paths through said generally planar common radiation output wherein at least two of said light emitting diodes are disposed such that their outputs are along paths which intersect at a first focal point and wherein further there is at least a third additional light emitting diode whose output is along a path which avoids said first focal point such that the plurality of divergent paths cooperate to generate a position insensitive optical field for curing said dental composition.

2. The device according to claim 1, wherein said plurality of light emitting diodes comprises 4 light emitting diodes.

3. The device according to claim 1, wherein said plurality of light emitting diodes includes a first pair of light emitting diodes mounted a first distance from said generally planar common radiation output of said radiation source and a second pair of light emitting diodes mounted a second distance from said generally planar common radiation output of said radiation source, said second distance being greater than said first distance.

4. The device according to claim 3, wherein said second distance is greater than said first distance by from about 0.5 mm to about 2 mm.

5. The device according to claim 4, wherein said second distance is greater than about said first distance by about 1 mm.

6. The device according to claim 3, wherein each of said light emitting diodes is mounted about said assembly axis at an angle of from about 10° to about 30°.

7. The device according to claim 6, wherein each of said light emitting diodes is mounted about said assembly axis at an angle of about 20°.

8. The device according to claim 1, further comprising a lens, the outer surface of which lens defines said generally planar common radiation output of said radiation source.

9. The device according to claim 8, wherein said lens is an aspherical lens.

10. The device according to claim 1, wherein each of said light emitting diodes has a characteristic maximum luminous power output and said power supply is adapted to operate each of said light emitting diodes at a luminous power output of at least about 85 percent of its maximum luminous power output.

11. The device according to claim 1, wherein said position insensitive optical field is generally uniform over an axial distance of from about 1 to about 5 mm from said radiation output of said radiation source.

12. The device according to claim 1, wherein said plurality of light emitting diodes comprises 4 light emitting diodes such that a first and second light emitting diode are each disposed such that their outputs are along paths which intersect at a first focal point and further there are third and fourth light emitting diodes whose outputs intersect at a second focal point.

13. A method of curing a photosensitive dental composition curable by way of irradiation with light of predetermined wavelength comprising:
   applying said photosensitive dental composition to a dental surface, or a cavity; and
   irradiating said dental composition with a position insensitive optical held generated by way of an irradiation source including an axial array of light emitting diodes, wherein said axial array of light emitting diodes comprises a plurality of light emitting diodes mounted about an assembly axis defined thereby at a plurality of axial distances from a generally planar common radiation output of said radiation source and being further characterized in that said plurality of light emitting diodes arc directed along a plurality of divergent paths through said generally planar common radiation output of said radiation source wherein at least two of said light emitting diodes are disposed such that their outputs are along paths which intersect at a first focal point and wherein further there is at least a third additional light emitting diode whose output is along a path which avoids said first focal point such that the plurality of divergent paths cooperate to generate a position insensitive optical field.

14. The method according to claim 13, wherein said plurality of light emitting diodes includes 4 light emitting diodes.

15. The method according to claim 13, wherein said plurality of light emitting diodes includes a first pair of light emitting diodes mounted a first distance from said generally planar common radiation output and a second pair of light emitting diodes mounted a second distance from said generally planar common radiation output of said radiation source, said second distance being greater than said first distance.

16. The method according to claim 15, wherein said second distance is greater than said first distance by about from 0.5 mm to about 2 mm.

17. The method according to claim 16, wherein said second distance is greater than said first distance by about 1 mm.

18. The method according to claim 15, wherein each of said light emitting diodes is mounted at an angle of from about 10° to about 30° to said assembly axis.

19. The method according to claim 13, wherein said radiation source includes a lens, the outer surface of which defines the radiation output of said radiation source.

20. The method according to claim 19, wherein said lens is an aspherical lens.

21. A device for curing a photosensitive dental composition curable by way of irradiation with light of predetermined wavelength comprising:

(a) a power supply; and (b) a radiation source coupled to said power supply and powered thereby, said radiation source including an axial array of light emitting diodes and having a generally planar common radiation output and wherein said axial array of light emitting diodes comprises a plurality of light emitting diodes mounted about an assembly axis defined thereby at a plurality of axial distances from said generally planar common radiation output of said radiation source and being further characterized in that said plurality of light emitting diodes are each mounted and fixed relative to a head assembly about said assembly axis at an angle so as to be directed along a plurality of divergent paths through said generally planar common radiation output wherein at least two of said light emitting diodes are disposed such that their outputs are along paths which intersect at a first focal point and wherein further there is at least a third additional light emitting diode whose output is along a path which avoids said first local point such that the diodes cooperate to generate a position insensitive optical field for curing said dental composition.

22. A device for curing a photosensitive denial composition curable by way of irradiation with light of predetermined wavelength comprising:

(a) a power supply; and (b) a radiation source coupled to said power supply and powered thereby, said radiation source including an axial array of light emitting diodes and having a generally planar common radiation output, wherein said axial array of light emitting diodes comprises a plurality light emitting diodes mounted and fixed relative to a head assembly about an assembly axis defined thereby at a plurality of axial distances from said radiation output of said radiation source and being further characterized in that said plurality of light emitting diodes are directed along a plurality of divergent paths through said generally planar common radiation output wherein at least two of said light emitting diodes are disposed such that their outputs are along paths which intersect at a first focal point and wherein further there is at least a third additional light emitting diode whose output is along a path which avoids said first focal point such that the plurality of divergent paths cooperate to generate a position insensitive optical field for curing said dental composition.

23. A method of curing a photosensitive dental composition curable by way of irradiation with light of predetermined wavelength comprising:

applying said photosensitive dental composition to a dental surface, or a cavity; and irradiating said dental composition with a position insensitive optical field generated by way of an irradiation source including an axial array of light emitting diodes, wherein said axial array of light emitting diodes comprises a plurality of light emitting diodes mounted and fixed relative to a head assembly about an assembly axis defined thereby at a plurality of axial distances from a generally planar common radiation output of said radiation source and being further characterized in that said plurality of light emitting diodes are directed along a plurality of divergent paths through said generally planar common radiation output of said radiation source wherein at least two of said light emitting diodes are disposed such that their outputs arc along paths which intersect at a first focal joint and wherein further there is at least a third additional light emitting diode whose output is along a path which avoids said first focal point such that the plurality of divergent paths cooperate to generate a position insensitive optical field.

* * * * *